(12) United States Patent
Neas et al.

(10) Patent No.: US 8,080,422 B2
(45) Date of Patent: Dec. 20, 2011

(54) METHOD OF GENERATING A FLUID STREAM IN A MICROFLUIDIC DEVICE

(75) Inventors: Edwin Dean Neas, Nunn, CO (US); Jerald Edward Kuiken, Windsor, CO (US); John Louis Schenk, Fort Collins, CO (US); Thomas Boyd Gilligan, College Station, TX (US)

(73) Assignee: XY, LLC, Navasota, TX (US)

( * ) Notice: Subject to any disclaimer, the term of this patent is extended or adjusted under 35 U.S.C. 154(b) by 0 days.

(21) Appl. No.: 12/807,231

(22) Filed: Aug. 31, 2010

(65) Prior Publication Data
US 2011/0000934 A1 Jan. 6, 2011

Related U.S. Application Data

(62) Division of application No. 11/004,382, filed on Dec. 3, 2004, now abandoned.

(51) Int. Cl.
*G01N 15/10* (2006.01)
(52) U.S. Cl. ............... 436/43; 436/52; 436/63; 436/180
(58) Field of Classification Search .................... 422/99, 422/100, 101, 505; 436/43, 52, 63, 180
See application file for complete search history.

(56) References Cited

U.S. PATENT DOCUMENTS

| | | |
|---|---|---|
| 3,756,459 A | 9/1973 | Bannister et al. |
| 4,796,788 A | 1/1989 | Bond |
| 5,492,534 A | 2/1996 | Athayde et al. |
| 5,559,032 A | 9/1996 | Pomeroy et al. |
| 5,665,315 A | 9/1997 | Robert et al. |
| 5,690,815 A | 11/1997 | Krasnoff et al. |
| 5,799,830 A | 9/1998 | Carroll et al. |
| 5,888,823 A | 3/1999 | Matsumoto et al. |
| 5,893,843 A | 4/1999 | Rodrigues Claro |
| 5,919,360 A | 7/1999 | Contaxis, III et al. |
| 5,934,885 A | 8/1999 | Farrell et al. |
| 6,086,574 A | 7/2000 | Carroll et al. |
| 6,328,071 B1 | 12/2001 | Austin |
| 6,495,366 B1 | 12/2002 | Briggs |
| 6,698,627 B2 | 3/2004 | Garcia et al. |
| 6,729,369 B2 | 5/2004 | Neas et al. |
| 6,752,298 B2 | 6/2004 | Garcia et al. |
| 6,761,286 B2 | 7/2004 | Py et al. |
| 6,761,288 B2 | 7/2004 | Garcia |
| 6,789,706 B2 | 9/2004 | Abergel et al. |
| 6,789,750 B1 | 9/2004 | Helt |
| 2002/0096123 A1* | 7/2002 | Whittier et al. ............... 119/174 |
| 2005/0011582 A1 | 1/2005 | Haug |
| 2006/0118167 A1 | 6/2006 | Neas et al. |

OTHER PUBLICATIONS

U.S. Appl. No. 11/004,382, filed Dec. 3, 2004, entilted "Pressure Regulated Continuously Variable Volume Container for Fluid Delivery".

Provisional U.S. Appl. No. 60/669,912, filed Apr. 7, 2005 entitlted "Flow Path Conditioner System".

(Continued)

*Primary Examiner* — Jan Ludlow
(74) *Attorney, Agent, or Firm* — Craig R. Miles; CR Miles, P.C.

(57) ABSTRACT

A method of continuously regulating external gas pressure on a variable volume container for the delivery of fluids to a microfluidic device and analysis of particles based upon relative presence or absence of at least one particle characteristic.

19 Claims, 8 Drawing Sheets

OTHER PUBLICATIONS

Non-Provisional U.S. Appl. No. 11/400,839, filed Apr. 6, 2006 entilted "Flow Path Conditioner System".
PCT International Patent Application No. PCT/US2006/013082, filed Apr. 6, 2006, entitled "Flow Path Conditioner System".
U.S. Appl. No. 11/804,879, filed May 21, 2007, entilted "Antimicrobially Active Compositions".
U.S. Appl. No. 11/901,915, filed Sep. 19, 2007, entitled "Differential Evaporation Potentiated Disinfectant System".
PCT International Patent Application No. PCT/US2008/010684, filed Sep. 12, 2008, entitled "Differential Evaporation Potentiated Disinfectant System".

* cited by examiner

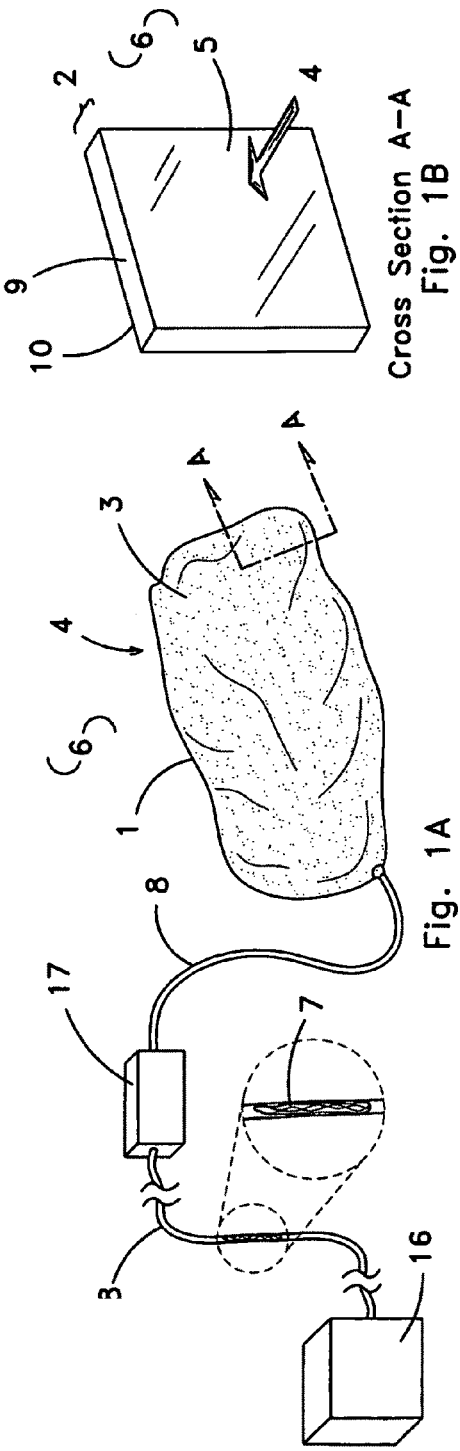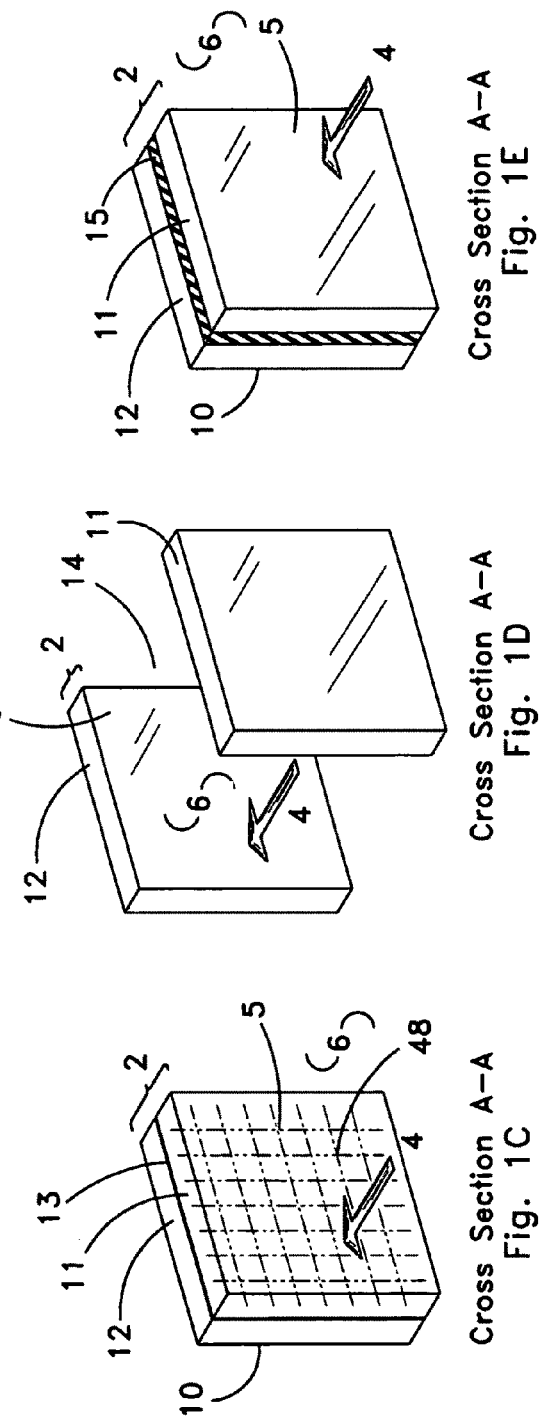

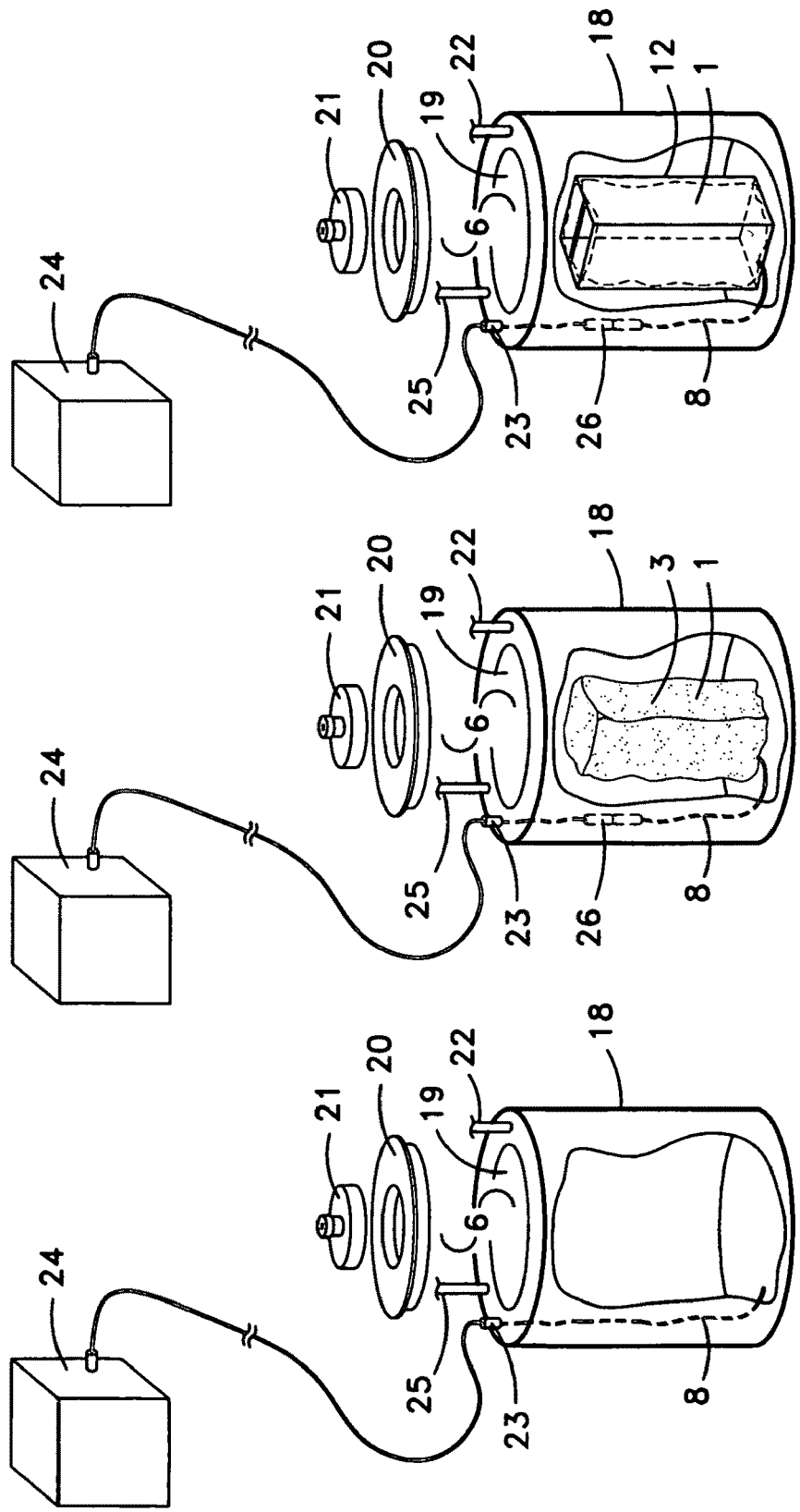

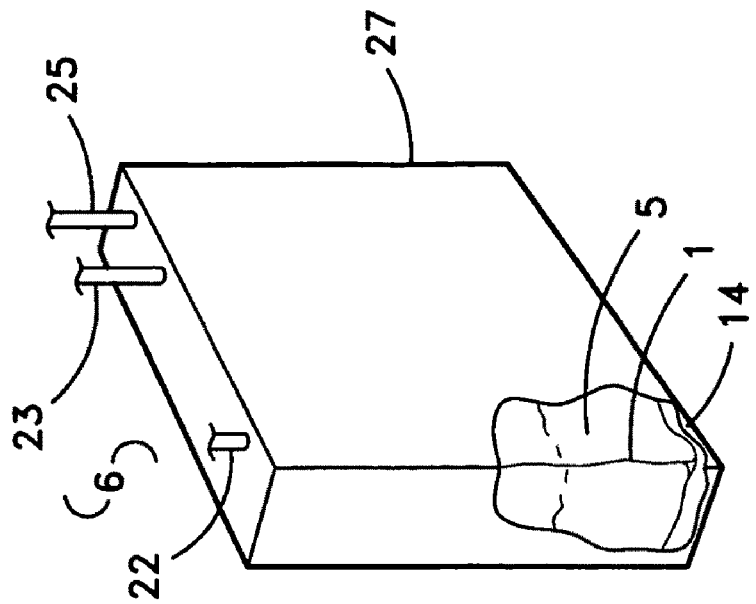
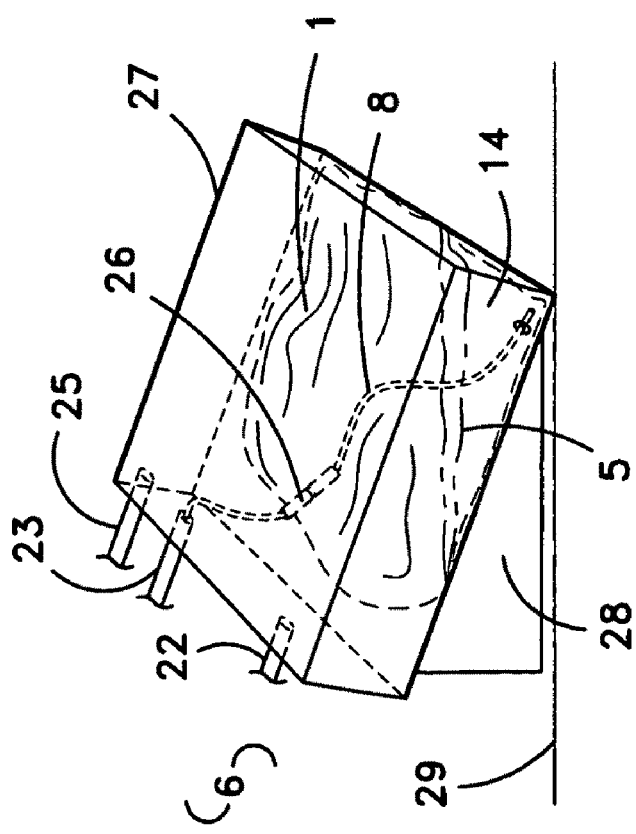

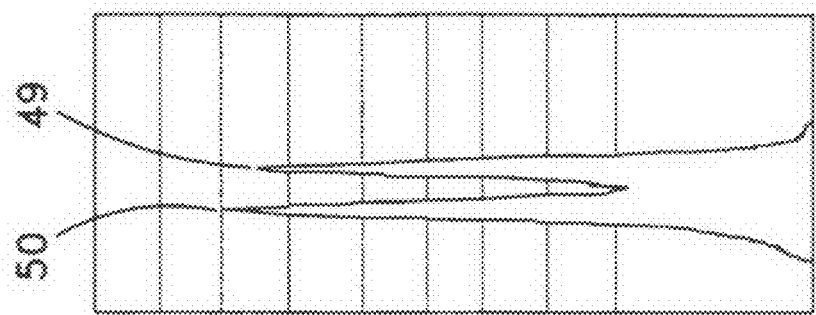
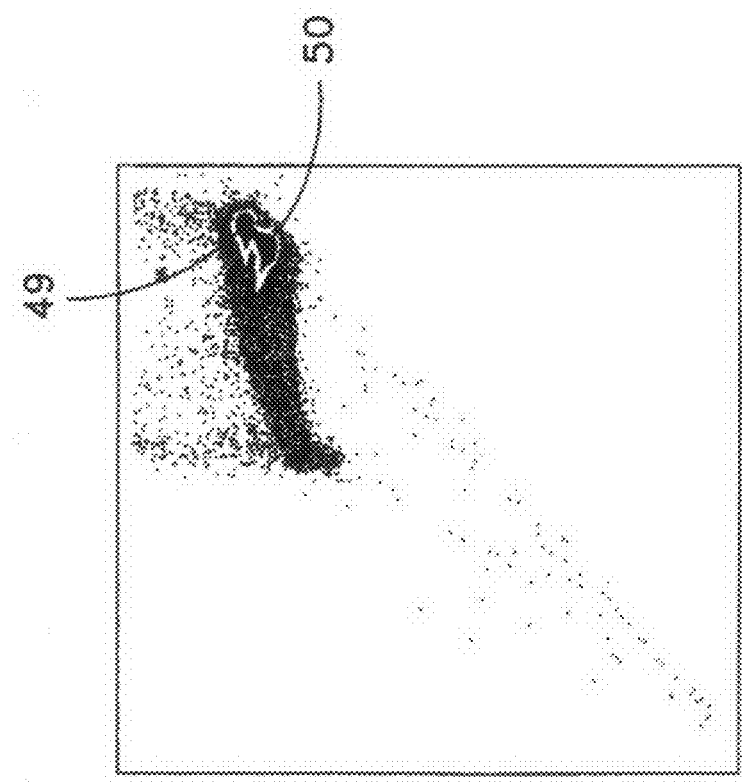
Fig. 6

METHOD OF GENERATING A FLUID STREAM IN A MICROFLUIDIC DEVICE

This Application is a division of U.S. patent application Ser. No. 11/004,382, filed Dec. 3, 2004, now abandoned, hereby incorporated by reference herein.

I. BACKGROUND

A pressure regulated continuously variable volume container for the handling and delivery of fluids. Specifically, a pressure regulated variable volume container useful in generating a fluid stream in the flow path of various types of microfluidic devices such as flow cytometers or liquid chromatographs.

Flow cytometry, liquid chromatography, and other microfluidic devices are prominent tools used in basic and applied research and in commercial manufacturing processes. These microfluidic systems are routinely used to analyze, separate, isolate, or purify biological particles, such as cells, organelles, chromosomes, deoxyribonucleic acids (DNA), ribonucleic acids (RNA), DNA fragments, RNA fragments, proteins, protein fragments, peptides, oligonucleotides, or the like.

Specifically with respect to applications in flow cytometry or the utilization of flow sort devices, biological particles, such as cells (which may be modified with one or a plurality of types or kinds of ligands, labels, or fluorescent dyes), or carrier particles (which can bear biological particles such as antibodies or oligonucleotides, or the like), can be analyzed and sorted to isolate individual cells or biological particles, or subpopulations of cells or biological particles, having one or a plurality of common characteristic(s). As the field of flow cytometry has matured, an increased emphasis has been placed on retaining the biological function(s) of isolated cells or biological particles.

Flow cytometers can also be used to analyze and sort a mixture of non-biological particles. For example, non-biological particles may be differentially modified with analyte specific reagents and reacted with a heterogeneous mixture of biological particles or analytes. The non-biological particles loaded with the corresponding reagent specific biological particles or analytes can then be differentiated and isolated with the flow sort system. Flow sort applications of this type can provide epitope or gene sequence analysis similar to that of a microarray analysis which utilizes a flat surface, such as a microscope slide, to present different analyte specific reagents such as antibodies, oligonucleotides, aptamers, or the like, to one or more biological particles of a heterogeneous biological mixture.

To maintain the biological function(s) of living cells during analysis, separation, purification, or collection, cells are entrained in fluids prepared to have certain characteristics relating to, purity, pH, ion concentration, osmolality, buffering capacity, nutrient availability, and the like. With respect to certain applications, these fluids must be prepared with water validated to be free of adventitious agents, pyrogens, or the like; or with chemicals obtained from chemical suppliers validated as in compliance with regulatory specifications such as cGMP guidelines, 510K guidelines, ISO-9000 type guidelines, batch record documentation, drug master file documentation, or the like.

Specifically with respect to chromatographic systems, the fluids used to entrain and separate biological particles are often purified mixtures of solvents and solutes in water. Variable mixture between two or more fluids to establish differential gradients of salt concentration, pH, solvent ratios, or the like may be utilized to selectively release particles from a variety of solid substrates to effect the separation of biological particles into subpopulations based upon one or more particle characteristics.

Characteristic of chromatographic systems is the relatively large volume of fluid used to separate mixtures of different particle(s) or population(s) of particles into individual particles or purified subpopulations of particles which are then isolated in a relatively small volume of fluid. Typically, many liters of an elution buffer may be collected in a plurality of individual fractions each containing just a few milliliters with the desired product isolated in one or few of such fractions. The preparation and handling of fluids to support chromatographic applications must be performed reliably by appropriately trained technicians. Any inaccuracy in the preparation of such fluids can lead to significant loss of chromatograph operating time or loss in whole or in part of the unpurified mixed particle(s) or population(s) of particles or of the purified individual particle(s) or subpopulation(s) of particles of interest.

Understandably, extensive research has been conducted resulting in numerous and varied types of microfluidic devices, fluids utilized with such microfluidic devices, and methods of making and using such microfluidic devices to separate biological and non-biological particles as above-described, or otherwise. Nonetheless, significant problems remain unresolved with regard to establishing and maintaining consistency in the preparation, handling, and delivery of fluids to and in the conduits of such microfluidic devices.

A significant problem with conventional delivery of fluids to microfluidic devices can be contamination of the fluid. The transfer of fluid from a fluid reservoir to a microfluidic device, and further transfer of the fluid through the various analytical conduits may require generation of hydrostatic pressure. Typically, a pump supplies the hydrostatic pressure required to move a fluid to and in the conduits of a microfluidic device.

Positive displacement pumps, for example, take up fluid from one side of the pump body, and utilizing valves, pistons, rotors, paddles, or the like, force the fluid to the other side of the pump. In this process, the fluid may come into contact with the internal surfaces of the pump depositing non-biological or biological materials, microbial or other infectious agents, which may remain within the body of the pump. In this way, the surfaces of the pump body can become a source of contamination to the subsequent volume of fluid transferred through the pump body.

Peristaltic pumps, apply pressure to the exterior surface of a conformable conduit to act on fluids contained within the conformable conduit. Peristalsis of the conformable conduit transfers fluid in one direction within the body of the conformable conduit. An advantage of the peristaltic pump can be that fluids do not contact the surfaces of the peristaltic pump. However, peristaltic pumps have disadvantages in that they may not build very high pressures, may tend to create oscillating hydrostatic pressure variations, may be expensive to build and maintain, and recurring peristalsis of the conformable conduit can cause progressive deformation or degradation of the conduit material which can shed, bleed, or leach into the fluid.

Another significant problem with conventional delivery of fluids to microfluidic devices can be the use of a gas or mixtures of gases, such as air, argon, nitrogen, helium, or the like, to pressurize the head space of a fluid reservoir to initiate and maintain a fluid stream in the conduits of the microfluidic device. Use of pressurized gas(es) or atmospheric gas pressure in contact with fluid in the reservoir can result in bubble formation in the fluid paths of the device. Since microfluidic devices have small diameter flow paths and the biological particles entrained in the fluid stream are also of small size, even very small or fine bubbles formed in the flow path can affect volume and laminar flow of the fluid within the flow paths, can cause failure of certain types of pumps, and can result in analytical errors. Even bubbles invisible to the naked eye can be problematic with respect to the proper performance of a microfluidic device.

One mechanism by which unwanted bubbles may spontaneously form in the flow path of a microfluidic device can be a change in the concentration of dissolved gas in the liquid stream followed by bubble formation. For example, a sheath fluid reservoir may contain an amount of sheath fluid to operate a flow cytometer for a long duration of time, sometimes in excess of 72 hours. With a head pressure of more than four atmospheres, or in certain applications in excess of 6 atmospheres, dissolved nitrogen content of the fluid can dramatically increase as the gases in the liquid move toward equilibrium with the gases in the head space of the reservoir.

Subsequently, when gas pressure on the liquid is reduced, bubbles may form. Reduction in gas pressure may come from operator inspection or manipulation of the amount of fluid remaining in the sheath fluid reservoir. Alternately, as the fluid flows through the conduits of the microfluidic device, fluid pressure may become substantially lower to match the operating pressure of the microfluidic flow path. Under these conditions bubbles may form and travel within the flow path of the microfluidic device. Alternately, surface tension of the bubble may allow it to adhere to the surfaces of the analytical components of the microfluidic device. Adhered bubbles may further serve as nuclei of condensation where additional small bubbles fuse, or where additional dissolved gas may enter the bubble.

The position of such bubbles partitioning between a surface adherent phase, and the fluid suspended phase, is determined by the size of the bubble, and the rate of flux of the fluid at that point in the apparatus. Microfluidic devices, flow cells, and flow cytometers commonly present regions in the flow path where flow is not laminar, where flux rate is low, and where bubbles tend to form. For example, microfluidic devices may have filters which purposefully restrict the fluid flow to facilitate removal of unwanted particles or aggregates. Bubbles often collect on the upstream side of such filters, effectively reducing the surface area of filter available to the fluid. Also, because gas may easily move across a filter, as dissolved gas, or as bubbles which may be smaller than the exclusion dimension of the filter, bubbles may accumulate on the opposite side of the filter as well.

Unwanted bubbles may also form in a microfluidic device by direct transfer of pressurized gas into the flow path of the microfluidic device. For example, when conventional flow cytometry sheath fluid reservoirs run out of fluid, or when the amount of fluid is low and the reservoir is not level, or when the sheath fluid reservoir is bumped, tipped, or shaken, pressurized gas can directly enter the flow path of the device. When pressurized gas enters the flow path of a microfluidic device directly, the bubbles can be much larger and in certain circumstances can interrupt of the flow of fluid all together, alter flow characteristics, or remain located in the flow path of the microfluidic device. If the microfluidic device or flow path is not disposable, a significant amount of time may be needed to dislodge or flush unwanted bubbles from the flow path.

Another problem related to the use of pressurized gas in contact with liquids to generate a fluid stream in microfluidic devices can be an increased concentration of oxygen in solution. For example, live sperm cells in the presence of media containing energy sources may exhibit a metabolic rate limited by the content of dissolved oxygen. During and after flow sorting of sperm cells it may be advantageous to have a viable but low metabolic rate. High concentrations of dissolved oxygen may be generated by equilibration of the sheath fluid with pressurized gases containing oxygen and its use may result in detrimentally high metabolic rates in sperm cells during flow analysis or flow sort processes.

A similar problem with the use of atmospheric gases or pressurized gases in contact with fluids to generate a fluid stream can be increased amounts of water introduced into anhydrous solvents or other water sensitive fluids used within microfluidic devices.

Another similar problem with the use of atmospheric gases or pressurized gases in contact with fluids to generate a fluid stream can be reaction of the certain gases with the fluid or the particles entrained in the fluid.

Another significant problem with conventional preparation of fluids for use with microfluidic devices or chromatographic systems can be that the available water quality or chemical solvent quality may be unacceptably low from which to make standardized solutions for certain applications. While there are numerous and varied methods to increase water quality, the cost of use may be unacceptably high when the source water contains a certain level of one or a plurality of materials, substances, or pathogens. This problem can be exacerbated with the use of specialized fluids for applications in basic research, clinical cell based therapy, or pharmaceutical production which may require fluids of higher quality with respect to precision of formulation, lot to lot consistency, and freedom from unwanted contaminating materials, particles, inorganic and organic substances, pathogens, chemicals, or the like. Particularly, with respect to fluids which are buffered or provide carbon sources to maintain cell function, high quality water may be essential to prevent, or reduce to acceptably low levels, the growth of pathogens.

A number of these problems are identified by U.S. Pat. No. 6,729,369 to Neas, which are addressed by preparing large volumes of sterile specialized fluids at a single geographic location at which high quality water and chemicals are available. Flexible walled vessels are then used for transporting the prepared sterile specialized fluids to the location where the fluids are used. Neas et al. does not, however, address the problem of establishing a pressurized fluid stream in the flow path of any microfluidic devices such as a flow cytometer, liquid chromatograph, or the like.

Another significant problem with conventional delivery of fluids to microfluidic devices can be cleanup, disposal of unused amounts of fluid, and sterilization of fluid reservoirs. Flow cytometers can consume between about 200 milliliters to about 800 milliliters of sheath fluid per hour, and are typically operated between about one hour and twenty four hours for a single procedure. The sheath fluid tanks or reservoirs typically contain between about five and about ten liters of sheath fluid, and if a procedure is interrupted or finished, it is often inconvenient to save the unused sheath fluid in the sheath fluid reservoir for use in the same procedure at a later date, because the sheath fluid tank may be needed for other procedures, or the sheath fluid may support the growth of microflora or microfauna, if stored. Even if the sheath fluid is stored, it may often be held at between 4-10° C., and must then be re-equilibrated to warm temperatures before further use.

In the broad consumer markets many products are distributed as containers of fluid which are opened for use, and accordingly, the fluids in the container begin to interact with atmosphere. With respect to certain fluids, interaction with atmosphere can be detrimental to the stability or consistency of the fluid. For example, paint or other surface coating products may begin to cure when exposed to atmosphere by moving toward equilibrium with the volume of atmosphere in the container. As such, an unused portion of paint in a container may form a thin layer of film. Another example may be free radical mediated rancidification of food oils such as olive oil, polyunsaturated vegetable oils, or the like, accelerated by molecular oxygen.

Many fluids are distributed in small pressurized containers which deliver the fluid through an orifice that causes the fluid to disperse when it exits the container. Common examples are cans of spray paint, hair spray, deodorant, insecticide, pesticide, herbicide, or the like. A disadvantage of the small pressurized containers is that there are a limited number of acceptable propellants which are both inert to reaction with contained fluid(s), and yet benign to the environment.

For larger scale application, these fluids are typically contained in reusable reservoirs which can be pressurized with a hand pumps or with air compressors. In addition to the problems above-discussed with respect to interaction of gas with the fluids, there are additional disadvantages related to the safety of cleaning large containers of the remaining fluids and the disposal of the remaining fluids.

The instant invention provides fluid delivery devices and methods of fluid delivery which address each of the above mentioned problems with the conventional technology in the specific area of microfluidic devices as well as the broader consumer market.

II. SUMMARY OF THE INVENTION

Accordingly, a broad object of the invention can be to eliminate exposure of fluid(s) being delivered to the flow path of a microfluidic device or chromatography systems to external sources of contamination. One aspect of this object of the invention can be to isolate the fluids being delivered to the flow path of a microfluidic device from moving toward equilibrium with atmospheric gases, mixtures of gases, or partial pressures of gases whether at atmospheric pressure or at greater than atmospheric pressures. A second aspect of this object of the invention can be to isolate the fluids being delivered to the flow path of a microfluidic device from exposure to non-biological materials or surfaces, such as, pump surfaces, dust, cleaning compositions, or the like; or to biological substances or surfaces which may introduce pathogens, bacteria, viruses, spores, cells, proteins, nucleic acids, tissues, blood, semen, urine, feces, or the like. A third aspect of this object of the invention can be to maintain a sterile fluid to be delivered to the flow path of a microfluidic device.

Another broad object of the invention can be to provide a container which has a continuously adjustable volume with respect to the amount of fluid contained within so that a stream of the fluid can be delivered to a microfluidic device. One aspect of this object of the invention can be to provide a container which has continuously variable volume in response to pressure exerted on the exterior surface which allows the interior surface of the container to act upon the fluid contained within to generate a fluid stream at an outlet. A second aspect of this object of the invention can be to provide a flexible wall capable of withstanding a gas pressure of between about 70 pounds per square inch (psi) and 100 psi to generate a fluid stream in the flow path of a microfluidic device of about 25 psi to about 50 psi. Naturally, for certain applications the amount of pressure exerted on the flexible wall may be greater and for certain applications the amount of pressure may be less. A third aspect of this object of the invention can be to deliver from a container having continuously variable volume in response to the pressure exerted by an amount of gas or liquid a fluid stream to the flow path of a microfluidic device, such as a flow cytometer or liquid chromatograph, in which particles can be entrained for analysis, separation, purification, or otherwise manipulated as desired.

Another broad object of the invention can be to provide an improvement of, or retrofit to, conventional fluid reservoir technology which further includes a container which has a continuously adjustable volume with respect to the amount of fluid contained within so that a stream of the fluid can be delivered to a microfluidic device. One aspect of this object of the invention can be to retrofit conventional flow cytometer sheath fluid tanks to further include a container which has a continuously adjustable volume with respect to the amount of fluid contained within so that a stream of the fluid can be delivered to a flow cytometer. A second aspect of this object of the invention with respect to liquid chromatographs can be to retrofit conventional liquid phase reservoirs to further include a container which has a continuously adjustable volume with respect to the amount of fluid contained within so that a stream of the fluid can be delivered directly to the separation column or to the high pressure pump of the liquid chromatograph.

Another broad object of the invention can be to establish or maintain a desired concentration of a dissolved gas or gases in the fluid delivered in the flow path of a microfluidic device such that particles (whether biological or non-biological) are exposed to the concentration or level of gas(es) necessary or desired; or exposure of particles to certain unwanted gases, mixtures of gases, or partial pressures of gases, increased water content, or the like, can be avoided.

Another broad object of the invention can be to provide fluids which are prepared to conform to the specifications of a particular microfluidic device or method of using the microfluidic device and are transferred to a container having continuously variable volume in accordance with the invention. Such containers prepared at a first geographic location can then be shipped to numerous other geographic locations to maintain consistency of the fluids utilized by the microfluidic devices at each location.

Another broad object of the invention can be to provide a receptacle of substantially fixed configuration into which an amount of gas or liquid can be delivered to act on the surface of a container having variable volume to deliver fluid to the flow path of a microfluidic device. One aspect of this broad embodiment of the invention can be to provide a receptacle of substantially fixed configuration having a plurality of compartments allowing a plurality of fluids to be delivered simultaneously to one or more microfluidic devices or containers.

Another broad embodiment of the invention can be to provide a flow cytometer device or chromatographic system and methods of using such flow cytometer device or chromatographic system which utilize fluids separated from the surfaces of the sheath fluid tank, and the gases delivered to the sheath fluid tank.

Another broad object of the invention can be to provide fluids and methods of delivering fluids to the flow paths of microfluidic devices which are compatible with the isolation or purification of cells or other particles or substances for reintroduction into a human or animal. There are a significant number of concerns raised with respect to the prevention of transmission of infection or disease when cells, particles or substances are isolated by microfluidic devices. Infectious particles or other agents can vary in size from prions which can be a few tens of nanometers, to virus particles which may be a few hundreds of nanometers, to yeasts, fungus, molds and bacteria which can be several hundreds of nanometers to many micrometers in size. Once a sample of cells, particles or other substance is contaminated with such infectious particles, it can be very difficult to remove them. In some cases, agents such as preservatives or antibiotics are acceptable, but in most products being used in animals and humans, the governmental regulations requires use of production methods which can be validated to produce biological cells, particles, substances or chemicals free of all such adventitious infectious particles or agents. The instant invention facilitates the preparation, shipment, storage, handling, and use of validated sterile solutions free of adventitious particles or agents, which can be delivered under pressure to flow cytometer, flow cell, or other microfluidic devices or chromatographic systems to generate cells, particles or other substances free of infectious or other unwanted agents.

Specific examples of such treatments or therapies can be, the isolation of specific hematopoetic stem cells from bone marrow with the proceeding separation of cancerous or abnormal cells from normal cells, and the reinsertion of the non-cancerous or normal cells back into the bone marrow; the isolation of certain white blood cells or blood cancer cells and the modification of such cells with certain conjugates and adjuvants which allow the cells to be re-inserted (dead or alive) as a form of therapeutic vaccination; the isolation of very rare cells, such as fetal cells, from the blood, such as maternal blood, containing a very small number of said fetal cells, for the purpose of performing genetic analysis such as polymerase chain reaction (PCR), genotyping, or haplotyping of such fetal cells, with minimal genetic background from the much more abundant genetic content of the maternal blood cells; the isolation of cells such as sperm cells from the vaginal fluids for the purposes of analyzing genetic make-up of the sperm cells; the flow sorting of sperm cells of mammals to generate enriched X-chromosome bearing and Y-chromosome bearing populations of viable sperm or the flow sorting of sperm cells enriched for certain genetic traits for further use in assisted reproduction techniques such as in-vitro fertilization, intra-cytoplasmic sperm injection, artificial insemination, or the like.

Another broad object of the invention can be to provide a container which has a continuously variable volume with respect to an amount of conformable material contained within such that such conformable material such as: water, a fluid for a microfluidic device; a sheath fluid for flow cytometry; a food; a drink; a food ingredient; a drink ingredient; a liquid detergent; a liquid pesticide or herbicide; a pharmaceutical solvent such as rubbing alcohol; a toiletry product such as a shampoo, a body wash, a hairspray or hair gel; or the like, can be handled, delivered, flowed in the flow path of a conduit, or otherwise utilized with only the desired contact with the atmosphere or other partial pressures of gases and without release to the atmosphere or other partial pressures of gases, unless desired. One aspect of this embodiment is the provision of large variable volume containers which contain specialized concentrates which are useful in the processing industry which formulates and produces fluid products for consumers and may benefit from new methods for accurate and clean delivery of fluid products, at controlled amounts, into the products they are compounding.

Naturally, further objects of the invention are disclosed throughout other areas of the specification, drawings, and claims.

III. A BRIEF DESCRIPTION OF THE DRAWINGS

FIG. 1A shows an embodiment of the invention which provides a pressure regulated variable volume container which delivers a fluid stream in response to an amount of gas acting on the exterior surface.

FIG. 1B shows a cross section through the flexible wall of an embodiment of the pressure regulated variable volume container.

FIG. 1C shows a cross section through the flexible wall of alternate embodiment of the pressure regulated variable volume container.

FIG. 1D shows a cross section through the flexible wall of second alternate embodiment of the pressure regulated variable volume container.

FIG. 1E shows a cross section through the flexible wall of third alternate embodiment of the pressure regulated variable volume container.

FIG. 2A shows a conventional sheath fluid tank for the delivery of sheath fluid(s) to a flow cytometer.

FIG. 2B shows an embodiment of the invention for the delivery of sheath fluid(s) to a flow cytometer in which a conventional sheath fluid tank is retrofitted to receive an amount of gas which acts upon the exterior surface of a variable volume container.

FIG. 2C shows an alternate embodiment of the invention for the delivery of sheath fluid(s) to a flow cytometer in which a conventional sheath fluid tank is retrofitted to receive an amount of gas which acts upon the exterior surface of a variable volume container.

FIG. 3A shows an embodiment of the invention in which a receptacle of substantially fixed configuration receives an amount of gas which acts upon the exterior surface of a variable volume container.

FIG. 3B shows an alternate embodiment of the invention in which a receptacle of substantially fixed configuration receives an amount of gas which acts upon the exterior surface of a variable volume container.

FIG. 6 shows a bivariate plot of sperm cells entrained in a fluid stream generated in accordance with the invention differentiated into X-chromosome bearing and Y-chromosome bearing populations.

IV. DETAILED DESCRIPTION OF THE PREFERRED EMBODIMENTS

Figure 4A:
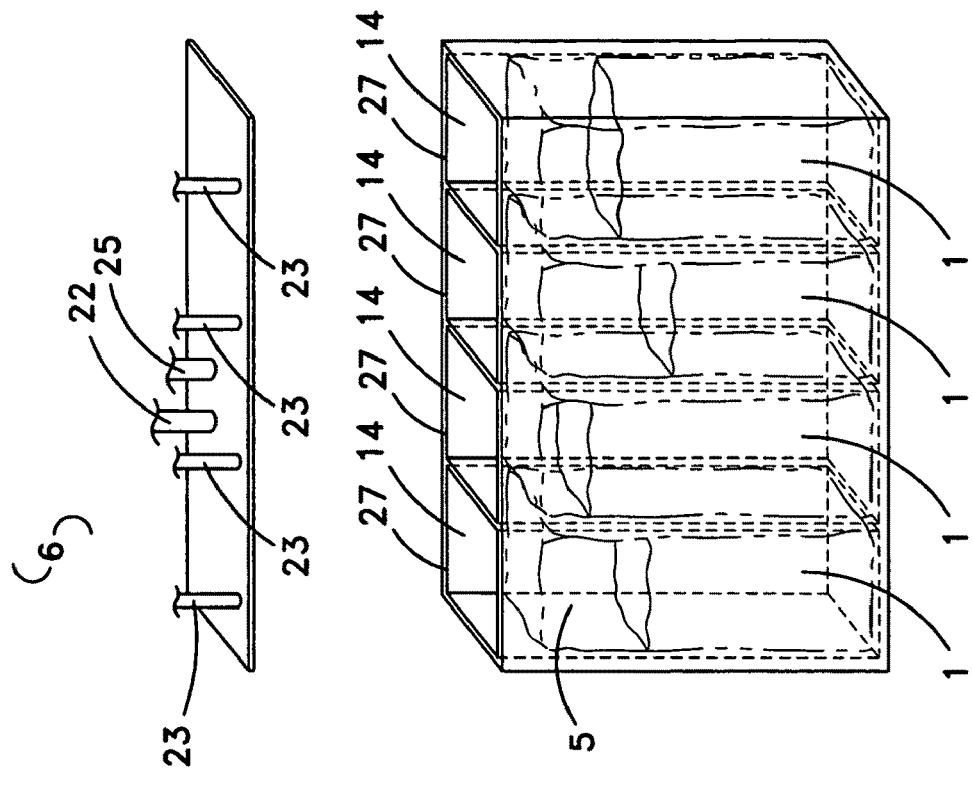
FIG. 4A shows an embodiment of the invention in which a plurality of receptacles each receive an amount of gas which acts upon the exterior surface of a variable volume container to generate a plurality of fluid streams.

Generally, an amount of fluid located within a variable volume container having a flexible wall which acts upon the amount of fluid in response to gas pressure exerted on the exterior surface to generate a fluid stream in the flow path of a conduit.

Now referring primarily to FIG. 1, an embodiment of the invention can provide a variable volume container (1) having a flexible wall (2) which acts on an amount of fluid (3) within the variable volume container (1) in response to an amount of pressure (4) exerted on the exterior surface (5) of the flexible wall (2) by an amount of gas (6). The amount of pressure (4) exerted on the exterior surface (5) of flexible wall (2) continuously adjusts the volume of the variable volume container (1) to act on the amount of fluid (3) to generate a fluid stream (7) (whether of continuous flow or of discontinuous flow) in the flow path of a conduit (8). As to certain embodiments of the invention the variable volume container (1) can in part be of substantially rigid configuration and in part a flexible wall (2). That portion of the variable volume container (1) which provides the flexible wall (2) can act on the amount of fluid (3) within the variable volume container (1) in response to the amount of pressure (4) exerted on the exterior surface (5) of the flexible wall by the amount of gas (6) to generate a fluid stream (7).

The fluid (3) within the variable volume container (1) broadly encompasses without limitation any fluid, liquid, composition, mixture, phase, product, or other material flowable in the flow path of the conduit (8) by continuous adjustment of the volume of the variable volume container (1) in response to the amount of pressure (4) exerted on exterior surface (5) of the flexible wall (2). The numerous and varied fluids flowable in the flow path of the conduit (8) (the flow path of the conduit includes numerous and varied configurations corresponding to the broad range of applications for the invention and without limitation includes microfluidic flow paths or conduits which typically have an internal diameter of about one millimeter or less) includes without limitation: water, a solvent, a solution, a buffered solution, a liquid chromatography solution, a fluid in which biological particles can be entrained, a fluid in which non-biological particles can be entrained, a fluid in which cells can be analyzed, a fluid in which sperm cells can be analyzed, a fluid in which sperm cells can be separated into Y-chromosome bearing and X-chromosome bearing populations, a flow cytometry sheath fluid, a flow cytometry sheath fluid in which non-biological particles can be entrained, a flow cytometry sheath fluid in which biological particles can be entrained, a flow cytometry sheath fluid in which cells are entrained, a flow cytometry sheath fluid in which spermatozoa can be entrained, a flow cytometry sheath fluid in which stained spermatozoa can be entrained, paint, pesticides, pastes, adhesives, organic solvents, pesticides, food products, beverages, and various permutations and combinations thereof.

Now referring primarily to FIG. 1B, the variable volume container (1) can provide a flexible wall (2) on which the amount of gas (6) exerts an amount pressure (4). The flexible wall (2) can comprise a layer of material (9) which has sufficient flexibility to adjust volume of the variable volume container (1) in response to the amount of pressure (4) exerted by the amount of gas (6) on the exterior surface (5). The layer of material (9) can be selected to provide an interior surface (10) compatible with the fluid (3) contained within the variable volume container (1) and to provide an exterior surface (5) compatible with the amount gas (6) which exerts the amount of pressure (4) thereon. With respect to certain embodiments of the invention, the layer of the material can further be selected to prevent or minimize the transfer of materials leachable or transferable from the layer of material (9) to the fluid (3) held by the variable volume container (1). The layer of material (9) can further be selected to prevent or minimize the transfer the amount of gas (6) through the layer of material (9) to the fluid held by the variable volume container (1). Without limiting the numerous and varied materials that can be used in accordance with the invention, preferred embodiments of the invention can utilize a layer of material (9) such as a polypropylene, a polyethylene, a nylon, a fluorocarbon, a styrene, a polycarbonate, a metal foil, a laminated paper, a biodegradable polymer, a waxed paper, or bonded layers thereof in various permutations and combinations. The layer of material (9) can include a coat of material, such as an oxygen barrier, a water barrier, alternate layers of a surface filling polymer and a ceramic (for example Barix), or the like.

Now referring primarily to FIG. 1C, as to other embodiments of the invention the flexible wall (2) can comprise two layers of material. The first layer (11) which establishes the exterior surface (5) compatible to the amount of gas (6) which exerts a pressure (4) on the flexible wall (2) and a second layer (12) providing an interior surface (10) compatible with the fluid (3) within the variable volume container (1). The first layer (11) can be selected from materials such as a polypropylene, a polyethylene, a fluorocarbon, a styrene, a polycarbonate, a Mylar® film, an oxygen barrier, a water barrier, or the like. The second layer (12) can be selected from the same or a different material then the first layer (11) such as a polypropylene, a polyethylene, a fluorocarbon, a styrene, a polycarbonate, a water barrier, or oxygen barrier (for example Barix), or the like. Either or both of the first layer (11) or the second layer (12) can be further include a reinforcement element (48) such as individual fibers, threads, strands, a net, web, or the like, which can be made of a reinforcement material such as a nylon, a cotton, a carbon fiber, a metal strand, a plastic strand, or the like.

As to certain embodiments of the invention, the first layer (11) and the second layer (12) of the flexible wall (2) can slidely engage, while as to other embodiments of the invention the first layer (11) and the second layer (12) can be fixedly engaged. Fixed engagement between the first layer (11) and the second layer (12) can be generated by the use of an adhesive layer (13), or other type of layer, or other process which induces a surface of the first layer (11) and a surface of the second layer (12) to adhere to each other.

Now referring primarily to FIG. 1D, as to other particular embodiments of the invention, a gas collection element (14) can be interposed between the first layer (11) and the second layer (12). As to these embodiments of the invention, the amount of gas (6) which exerts an amount of pressure (4) on the exterior surface (5) of the variable volume container (1) collects in the gas collection element (14) and exerts an amount of pressure (4) on the second layer (12) which acts on the liquid (3) contained within to generate the fluid stream (7). The first layer (11) acts to adjust the volume or pressure (or both) of the amount of gas (6) within the gas collection element (14) to the necessary or desired amount. As to these embodiments of the invention, in which the first layer (11) does not have to function as part of a flexible wall (2) of the variable volume container (1), the first layer (11) can have a substantially fixed configuration formed from a material such as a plastic, a fiberglass, a glass, a metal, a steel, a polycarbonate, an acrylic, a polypropylene, a vinyl, a fluorocarbon, a carbon fiber, or the like.

Now referring primarily to FIG. 1E, other embodiments of the invention can further include a flexible wall (2) having at least one intermediate layer (15) located between the first layer (11) and the second layer (12). The at least one intermediate layer (15) be can be selected from a material such as a polypropylene, a polyethylene, a fluorocarbon, a styrene, a polycarbonate, a Mylar® film, a ceramic layer, an oxygen barrier (or other gas), a water barrier, or the like. Additional embodiments of the invention can further provide the gas collection element (14) (similar to FIG. 1D) interposed between the first layer (11) and the at least one intermediate layer (15), or as to other particular embodiments of the invention the gas collection element (14) (similar to FIG. 1D) can be interposed between the second layer (12) and the at least one intermediate layer (15). Where the gas collection element (14) is interposed between the first layer (11) and the at least one intermediate layer (15), the first layer (11) can be of substantially fixed configuration as above-described. In those embodiments of the invention in which the gas collection element (14) is interposed between the second layer (12) and the at least one intermediate layer (15), either of the first layer (11) or the at least one intermediate layer (15), or both, can have a substantially fixed configuration, while the second layer (12) provides sufficient flexibility to allow the variable volume container (1) to continuously adjust volume in response to the amount of pressure (4) exerted by the amount of gas (6) on the flexible wall (2). As to those embodiments of the invention, in which the liquid (3) engages the interior surface (10) of the second layer (12) and the amount of gas (6) exerts an amount of pressure (4) on the exterior surface (5) of the first layer (11), then the first layer (11), the intermediate layer (15) and the second layer (12) can have sufficient flexibility to allow variable adjustable volume of the container (1) whether the surfaces of the layers have slidely or fixed engagement.

The amount of gas (6) which exerts an amount of pressure (4) on the exterior surface (5) of the flexible wall (2) to provide a continuously adjustable variable volume container (1) to act on the fluid (3) contained within can be any type or kind of gas (6) compatible with the exterior surface (5) of the flexible wall (2) on which it acts, such as, an atmosphere, a mixture of gases, a mixture of gases having selected partial pressures, a purified gas, a filtered gas, a conditioned gas, or the like. As to alternate embodiments of the invention, the amount of gas (6) can be replaced with an amount of flowable material capable of acting upon the exterior surface (5) of the flexible wall (2) to adjust the volume of the container (1), such as water, oil, or a solution.

With respect to certain embodiments of the invention, the gas (6) can exert an amount of pressure (4) on the exterior surface (5) of the flexible wall (2) of between 1 pound per square inch (psi) to about 500 pounds per square inch (psi). As to other embodiments of the invention utilized for flow cytometry applications, the amount of gas (6) can exert a pressure on the exterior surface (5) of the flexible wall (2) of between about 10 psi and about 200 psi. Alternately, the amount of gas (6) whether within the gas collection element (14), or otherwise, can be adjusted to generate a sufficient amount of pressure (4) on the exterior surface (5) of the flexible wall (2) of the variable volume container (1) to generate a fluid stream (7) within the flow path of a conduit (8) of a microfluidic device (16) having a fluid pressure of between 10 psi and about 200 psi, or a fluid pressure sufficient to generate a fluid stream (7) within the flow path of the conduit (8) having a velocity sufficient to entrain particles for a particular type or kind of application, analysis, differentiation, or separation.

Again referring primarily to FIG. 1A, particular embodiments of the invention can further include fluid pressure generator (17), such as a peristaltic pump, piston pump, or the like to generate sufficient pressure for certain microfluidic applications, or other applications, in the range of between about 100 psi and about 5000 psi. One illustrative embodiment of the invention, provides a microfluidic device (16) configured as a high pressure liquid chromatograph (HPLC) having a fluid pressure generator (17) which increases fluid pressure within the conduit (8) to between about 100 psi and about 3000 psi for applications such as normal phase or reverse phase liquid chromatography.

Now referring primarily to FIG. 2A, a conventional substantially cylindrical sheath fluid tank (18) (or other configuration of sheath fluid tank) can have an aperture element (19). The aperture element (19) of the sheath fluid tank (18) can be configured to mate with a removably sealable closure (20) which can further include a closure securement element (21) to secure the removably sealable closure (20). Alternate embodiments of the closure securement element (21) can include, as examples, mated spiral threads on the removable sealable closure (20) and the sheath fluid tank (18), spiral threaded rods connected to the sheath fluid tank which mate with spirally threaded hardware which operationally apply pressure to the removably sealable closure (20), straps, catches, or the like.

A gas inlet element (22) allows delivery of an amount of gas (6) (various types and kinds of gas(es) as above-described) to the interior of the sheath fluid tank (18). In conventional applications, an amount of fluid (3) is contained by the sheath fluid tank (18) and the amount of gas (6) delivered to the interior of the sheath fluid tank (18) exerts an amount of pressure (4) on the surface of the fluid (3). A portion of the fluid (3) under pressure flows through the fluid outlet element (23) to be delivered as a fluid stream (7) in the flow path of a flow cytometer (24) (or other microfluidic device). A pressure adjustment element (25) (such as a pressure relief valve) can allow for adjustment of the amount of pressure within the sheath fluid tank (18).

Now referring primarily to FIG. 2B, a conventional sheath fluid tank (18) (or similar fluid tank) can be adapted to operate in accordance with the invention. A variable volume container (1) having a flexible wall (2) can contain an amount of fluid (3)(sheath fluid for flow cytometry applications). The variable volume container (1) containing the fluid (3) can be located inside of the conventional sheath fluid tank (18) by transfer through the aperture element (19). A conduit (8) provides a flow path between the variable volume container (1) and the fluid outlet element (23). A coupler element (26) may be required to connect the conduit (8) to the fluid outlet element (23) of the sheath fluid tank (18). The coupler element can in certain instances comprise mated spirally threaded hardware which operates to compress a ferrule against a seat to seal the flow path within the conduit (8) from leaking fluid. Naturally, a variety of hardware can be used as the coupler element (26) to provide a continuous flow path to the fluid outlet element (23).

Now referring primarily to FIG. 2C, as to certain embodiments of the invention the variable volume container (1) can be enclosed by a second layer (12) of substantially fixed configuration as discussed above formed from a material such as a plastic, a fiberglass, a glass, a metal, a steel, a polycarbonate, an acrylic, a polypropylene, a vinyl, a fluorocarbon, a carbon fiber, a paperboard, a cardboard, or the like. The second layer can be sufficiently perforated or permeable to an amount of gas (6) to allow an amount of pressure (4) to be exerted on the exterior surface (5) of the flexible wall (2) to act upon the amount of liquid (3) or sheath fluid contained within to generate a fluid stream (7) within the flow path of the conduit (8).

Now referring primarily to FIG. 3A, certain embodiments of the invention can provide a receptacle (27) of substantially fixed configuration (rectangular as shown by FIG. 3A or otherwise as desired) in which one or more variable volume container(s) (1) having a flexible wall (2) can be located. The receptacle (27) may be mounted on a base (28) which orients the receptacle (27) relative to a support surface (29) (for example, angled as shown by FIG. 3A or substantially perpendicular to the support surface (29) as shown by FIG. 3B)

which can facilitate flow of the fluid (3) within the variable volume container (1) toward the conduit (8) which communicates with the fluid outlet element (23). The receptacle (27) of substantially fixed configuration can be made from a material such as a plastic, a fiberglass, a glass, a metal, a steel, a polycarbonate, an acrylic, a polypropylene, a vinyl, a fluorocarbon, a carbon fiber, or the like. A portion or the entirety of the receptacle (27) can be made from a material which allows visual observation of the variable volume container (1) and the fluid (3) within the variable volume container (1). The receptacle (27) can further include a gas inlet element (22) through which an amount of gas (6) can be introduced into the gas collection element (14) between the interior surface of the receptacle (27) and the exterior surface (5) of the variable volume container (1). A pressure adjustment element (25) can be further included to maintain the necessary or desired amount of gas pressure (4) exerted on the exterior surface (5) of the variable volume container (1).

Figure 4B:
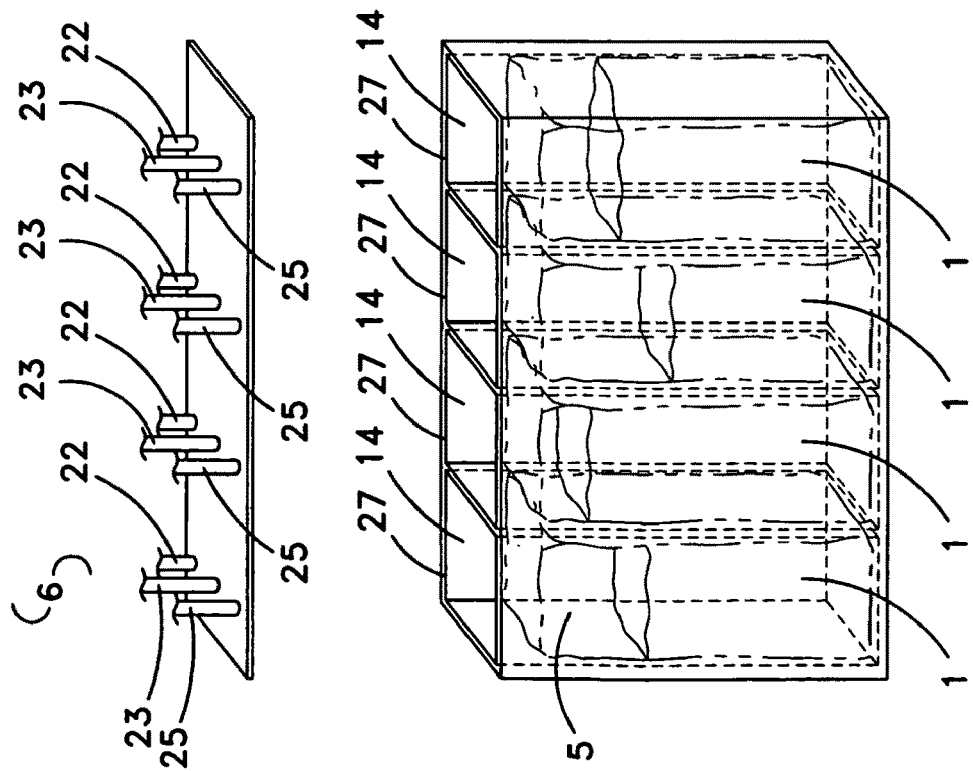
FIG. 4B shows an alternate embodiment of the invention in which a plurality of receptacles each receive an amount of gas which acts upon the exterior surface of a variable volume container to generate a plurality of fluid streams.

Now referring primarily to FIG. 4A, certain embodiments of the invention can include a plurality of receptacles (27), individually discrete or as a single integral piece (as shown by FIGS. 4A and 4B) providing a corresponding plurality of gas collection elements (14). FIG. 4A illustrates that each of the plurality of gas collection elements (14) can provide independent gas inlet elements (22), fluid outlet elements (23), and pressure adjustment elements (25) to allow each of the plurality of receptacle (27) to be utilized independent of the other receptacles (27). In this configuration of the invention, an amount of gas (6) can be delivered to each gas collection element (14) to establish an amount of pressure (4) on the exterior surface (5) of the flexible wall (2) of the variable volume container (1) located inside the individual receptacle (27). Accordingly, an amount of the fluid (3) contained in each of the variable volume containers (1) can be delivered to the fluid outlet element (23) from each receptacle (27). The fluid flow rate from each variable volume container (1) can be adjusted to be substantially the same or variably adjusted between receptacles (27).

Now referring primarily to FIG. 4B, alternate embodiments of the invention can provide a single gas inlet element (22) to deliver an amount of gas (6) to all the gas collection elements (14) to establish a substantially similar amount of gas pressure (4) on the exterior surface (5) of the flexible wall (2) of each of the plurality of variable volume containers (1) in the corresponding each of the plurality of receptacles (27) which can be adjusted by a single pressure adjustment element (25). Each receptacle can further provide a fluid outlet element (23) through which a fluid stream (7) can flow to the flow path of a microfluidic device (16) (similar to that shown in FIG. 1A).

Figure 5:
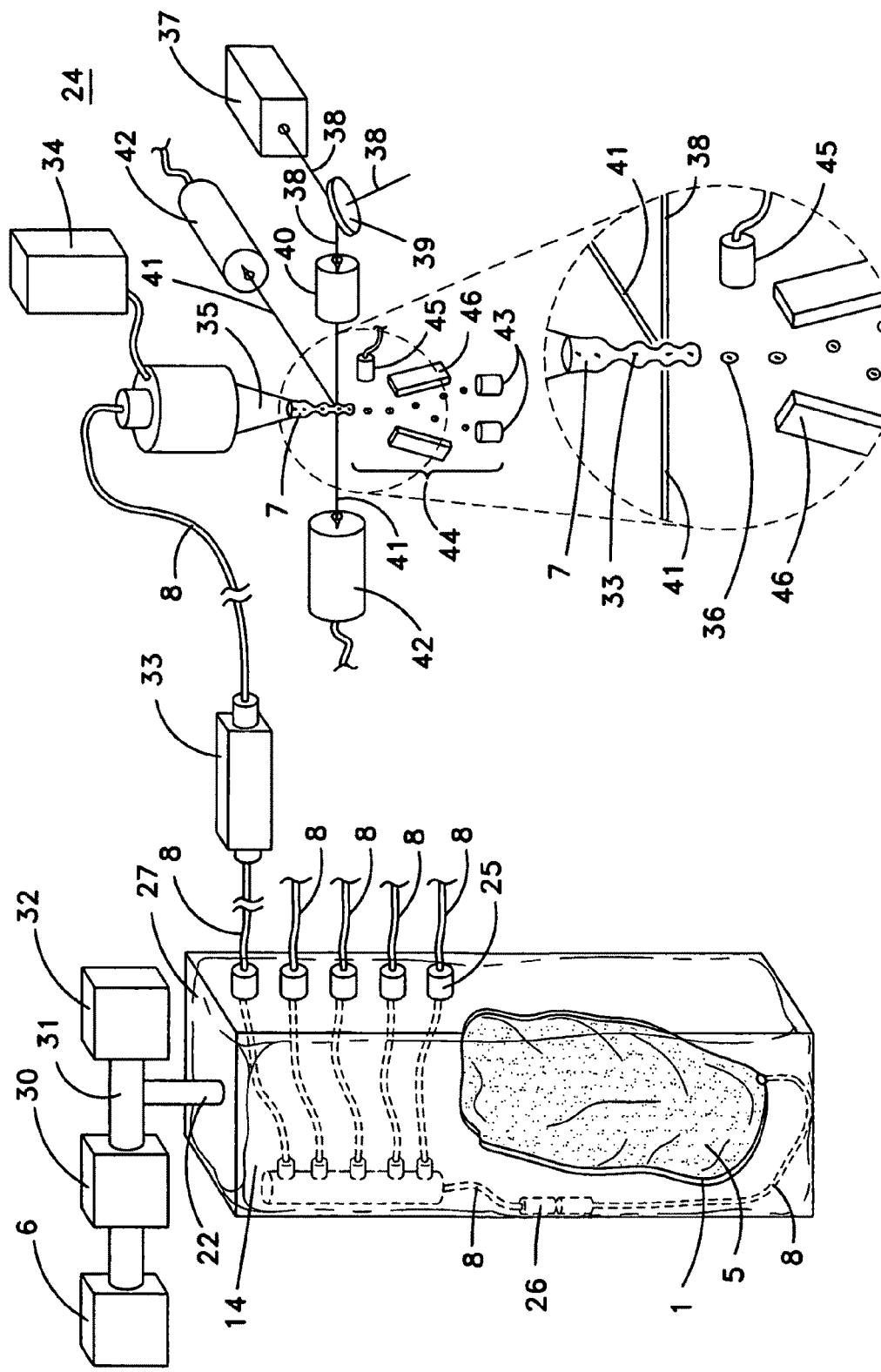
FIG. 5 shows a flow cytometer embodiment of the invention in which a fluid stream can be generated in the flow path of the flow cytometer from a variable volume container acted upon by an amount of gas.

Now referring primarily to FIG. 5, a generic microfluidics device in accordance with the invention is illustrated. An amount of gas (6) can be delivered with a pressure differential generator (30) such as a tank of pressurized gas, a gas compressor, or the like, to one or more gas inlet elements (22) of the receptacle(s) (27) through a gas transfer conduit (31). A pressure regulator (32) can be further included to regulate the pressure of the amount of gas (6) in the gas transfer conduit (31). The amount of gas (6) transfers from the gas inlet element (22) to a gas collection element (14) inside the receptacle (27) which can have a substantially fixed configuration as shown, or alternately described herein. At least one variable volume container (1) as above-described can be located inside the receptacle (27).

The amount of gas (6) within the gas collection element (14) acts upon the exterior surface (5) of the at least one variable volume container (1) located within the receptacle (27) to generate a fluid stream (7) at the fluid outlet element (25) which can be transferred within one or a plurality of conduits (8). The conduits (8) can have substantially the same internal diameter or varying internal diameters. The conduit (8) can further include a fluid conditioning element (33) such as a fluid filter, a gas scrubber, or a fluid pressure regulator, fluid pressure generator, such as a pump, or various permutations or combinations thereof. The conduit (8) can be connected to the flow path of a microfluidics device (24), such as a flow cytometer as shown in FIG. 5, or other microfluidic device, such as a fluid distribution device which transfers liquid(s) to and between locations on a liquid containment element such as plates having a plurality of wells, the surface of slides, cuvettes, channels, or other containment features.

As to the flow cytometer embodiment of the invention shown in FIG. 5, the fluid stream (7) can entrain particles (33) (as described above) delivered from a particle source (34). The fluid stream (7) having particles (33) entrained can be oscillated by a nozzle (35) to generate a plurality of droplets (36) below the nozzle (35). Each of the plurality of droplets (36) can entrain an individual particle (33). An illumination source (37), such as a laser, can emit a beam of light (38), or a plurality of beams of light can be generated by utilizing a beam splitting element (39) (or by utilizing a plurality of illumination sources (37)), which can be focused through an optical element (40) incident upon the particle (33) entrained in the fluid stream (7) below the nozzle (35), either as a single beam of light or a plurality of beams of light, whether at the same or different wave lengths. As to some embodiments of the invention, characteristics of the beam of light (38) can be altered by incidence upon the particle (33) within the fluid stream (7), and as to other embodiments of the invention the particle (or ligands, fluorescent materials, or the like, attached to the particle) can generate an emission (41). The beam(s) of light having altered characteristics or the emission (41) can be received by a single or a plurality of detectors (42) which can generate a signal for analysis to differentiate the particles (33) entrained in the droplets (36) based upon one or a plurality of particle characteristics. The differentiated particles can be separated based upon the presence or absence of one or a plurality of particle characteristics into individual collection elements (43). The separation device (44) can include a droplet charge generator (45) which induces a positive or negative charge in each droplet (36) and a droplet deflector (46) which acts upon the charged droplets to establish a trajectory to the proper collection element (43).

Now referring primarily to FIG. 6, a bivariate plot generated during the flow sort of spermatozoa into X-chromosome bearing and Y-chromosome bearing populations in accordance with the invention is shown. The bivariate plot shows that a mixture of X-chromosome bearing sperm cells and Y-chromosome bearing sperm cells can be resolved into first X-chromosome bearing population (49) and second Y-chromosome bearing population (50). Provision of the bivariate plot is not intended to be limiting with respect to the numerous and varied applications of the invention. Rather, the bivariate plot is intended to be illustrative of the broad range of applications in which the invention can be utilized.

Figure 7:
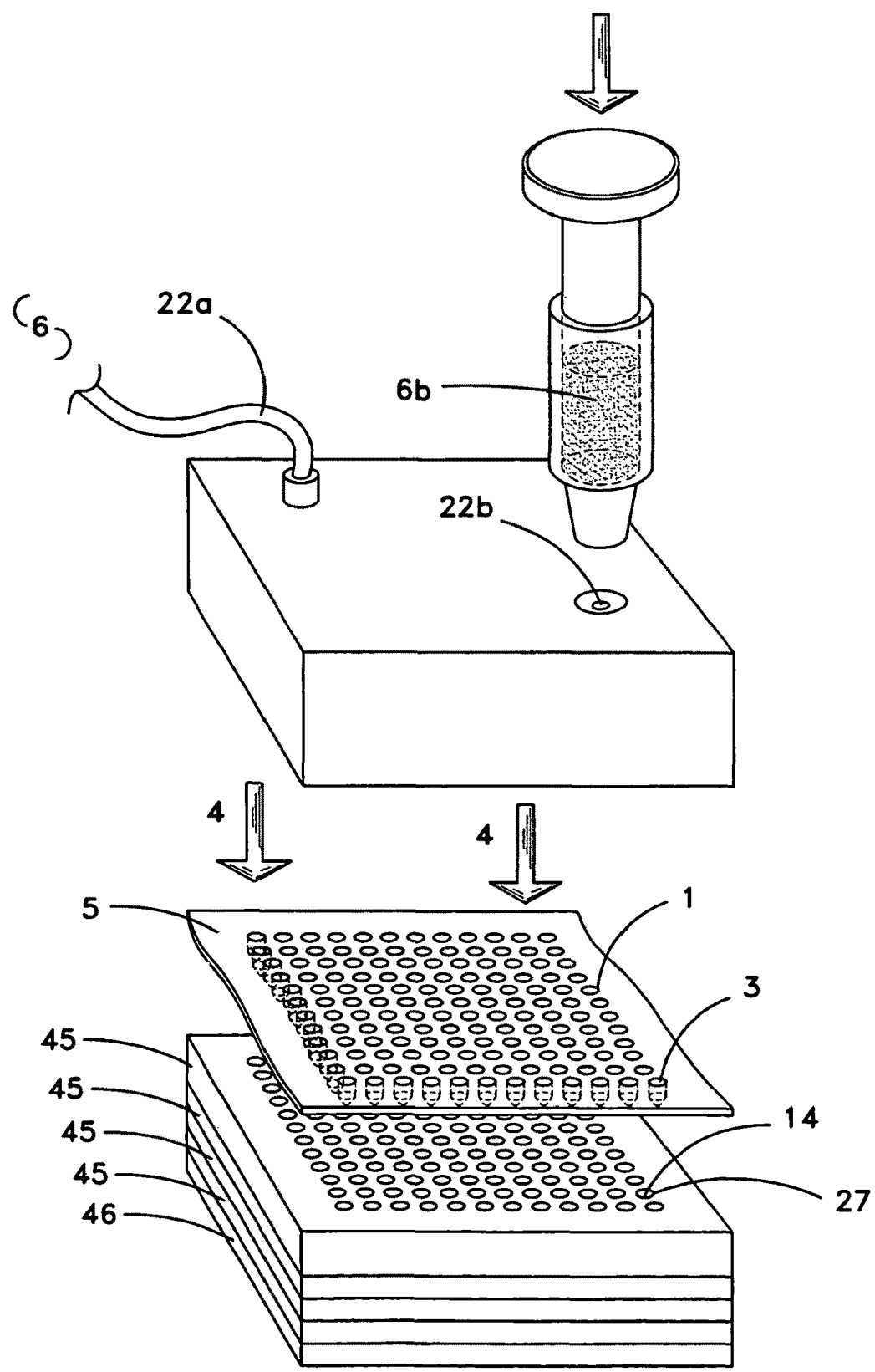
FIG. 7 shows an embodiment of the invention in which a plurality of variable volume containers each containing an amount of fluid are configured into a sheet of columns and rows.

Now referring primarily to FIG. 7, certain embodiments of the invention can provide a plurality of variable volume containers (1) configured as a single integral piece formatted in columns and rows, or otherwise as necessary or desired. A plurality of receptacles (27) configured as a single integral piece formatted in columns and rows can receive the plurality of variable volume containers (1). A releasably sealable closure (20) can be configured to isolate each of the plurality of variable volume containers (1). An amount of gas (6) can be delivered through a gas inlet element (22a)(22b) (two embodiments shown) to the gas collection element (14) within each separate receptacle (27), whether to a single receptacle of the plurality of receptacles or to a plurality of receptacles substantially simultaneously. The amount of gas (6) exerts an amount of pressure (4) on the flexible wall(s) (2) of the individual variable volume containers (1) to generate a fluid stream in one or a plurality of conduits (8) which communicate with each receptacle (27).

Figure 8:
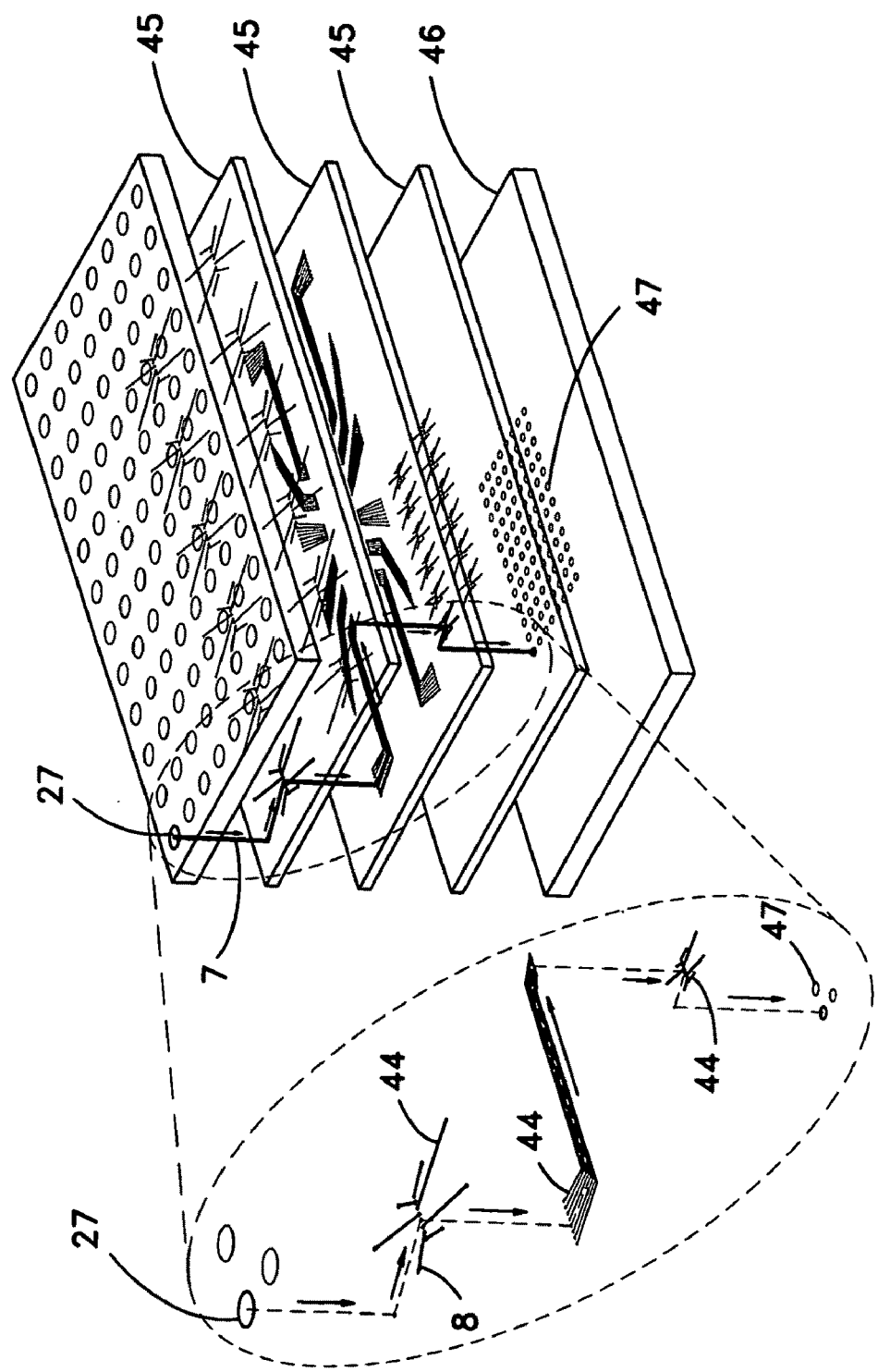
FIG. 8 illustrates a plurality of flow paths operable with the embodiment of the invention shown by FIG. 7.

Now referring primarily to FIG. 8, the conduit (8) which fluidicly communicates with each receptacle (27) can comprise a microfluidic conduit (internal diameter of one millimeter or less) such as a plastic tube, or as shown in FIG. 8 can also comprise a relief element (44) in the surface of a single or a plurality of fluid delivery bodies (45) which provides a flow path for the fluid stream (7). The fluid delivery bodies (45) can be releasably sealable and interchangeable to provide a number of different flow paths. In the embodiment shown, the flow path established by the releasably sealable fluid delivery bodies can deliver the fluid (3) from a plurality of variable volume containers (1) to a plate (46) having a plurality of wells (47).

V. Examples

Example 1

Now referring to FIG. 8, which shows a bivariate plot generated from the analysis of fluorochrome stained sperm cells differentiated based upon the presence of an X-chromosome or a Y-chromosome utilizing a DakoCytomation, Inc., MoFlo® flow cytometer in accordance with the invention. A conventional sheath fluid tank was retrofitted with a variable volume container in accordance with the invention containing about 5 liters of sterile sheath fluid. The sheath fluid was maintained at about 20° C. during use. An amount of gas was delivered to the sealed sheath fluid tank to exert an amount of gas pressure on the exterior surface of the variable volume container resulting in the generation of a fluid stream within the flow path of a DakoCytomation, Inc., MoFlo® flow cytometer. The flow cytometer was then otherwise operated in accordance with the standard operation procedures provided by DakoCytomation, Inc. for a period of about 8 hours to analyze and sort a mixture of sperm cells to generate a viable population of X-chromosome bearing spermatozoa and viable population of Y-chromosome bearing spermatozoa. X-chromosome bearing and Y-chromosome bearing populations enriched were established in discrete collection containers.

Example 2

Similarly, a flow cytometer sorting human sperm in accordance with the invention can provide X-chromosome bearing and Y-chromosome bearing populations for the purpose of sex selected artificial insemination. Human sperm cells sufficient for artificial insemination of a human female can be flow sorted in approximately 2 hours from male human ejaculate. The enriched X-chromosome bearing or Y-chromosome bearing sperm cell populations are typically over 80% pure. Clinical procedures may require that after each sample is sorted, the sorting fluidic channels are washed with an acid wash, a base wash, a disinfectant wash, and then a water wash. The instant invention can be used to deliver four different sterile fluids to the flow cytometer, and allows computer automated cleaning steps to be performed between patients. During the automated wash procedure, the physician may perform the artificial insemination procedure.

Example 3

In accordance with the invention, a plurality of different microfluidic devices can be operating 24 hours per day. The variable volume containers can be located in common receptacle pressured at about 1.6 atmospheres. Each microfluidic device can be served with one or more conduits from the variable volume containers which communicate with the conventional hardware of the microfluidic device.

As can be easily understood from the foregoing, the basic concepts of the present invention may be embodied in a variety of ways. The invention involves numerous and varied embodiments of a continuously variable volume container for fluid delivery and methods of making and using such continuously variable volume container.

As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of an "adjustable volume" should be understood to encompass disclosure of the act of "adjusting volume"—whether explicitly discussed or not—and, conversely, were there effectively disclosure of the act of "adjusting volume", such a disclosure should be understood to encompass disclosure of an "adjustable volume" and even a "means for adjusting volume." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the fluid delivery devices herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below are intended describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A method of flow cytometry, comprising the steps of:
   a. providing a variable volume container having a flexible wall;
   b. establishing an amount of fluid in said variable volume container;
   c. exerting an amount of pressure in the range of about 70 psi to 200 psi with an amount of a gas on an exterior surface of said flexible wall of said variable volume container;
   d. providing a conduit between said variable volume container and a flow path of a flow cytometer;
   e. generating a fluid stream of said amount of fluid in said flow path of said flow cytometer by exerting said amount of pressure with an amount of gas on said exterior surface of said flexible wall of said variable volume container having a fluid stream pressure of between 25 psi and about 50 psi;
   f. intermittently entraining a particle in said fluid stream in said flow path of said flow cytometer;
   g. generating oscillations in said fluid stream to establish a plurality of droplets;
   h. establishing said particle in one of said plurality of droplets;
   i. illuminating said particle in said one of said plurality of droplets for a duration of time;
   j. detecting an emission generated by said particle which varies based upon corresponding variation of at least one particle characteristic of said particle; and
   k. differentiating said particle based upon relative presence or absence of said at least one particle characteristic.

2. The method of flow cytometry as described in claim 1, wherein said step of providing a variable volume container comprises the step of providing a flexible tubular body having an upper end and a lower end each hermetically formed.

3. The method of flow cytometry as described in claim 1, wherein said step of providing a variable volume container having a flexible wall comprises the step of providing a container only a portion of which provides said flexible wall.

4. The method of flow cytometry as described in claim 1, further comprising the step of generating a said fluid stream from the group consisting of: a fluid flowable in the flow path of said flow cytometer, a water, a buffer, a sheath fluid, a flow cytometer sheath fluid, a liquid reagent, a cleaning solutions, and a solvent.

5. The method of flow cytometry as described in claim 1, where in said step of exerting an amount of pressure with an amount of gas on said flexible wall of said variable volume container further comprises selecting said amount of gas from the group consisting of an atmospheric gas, a mixture of gases, a mixture of gases having selected partial pressures, a purified gas, a nitrogen gas, a helium gas.

6. The method of flow cytometry as described in claim 1, wherein said step of intermittently entraining a particle in said fluid stream in said flow path of said flow cytometer comprises intermittently entraining a particle in said fluid stream selected from the group consisting of a cell, a sperm cell, a labeled sperm cell, a stained sperm cell, a component obtained from a cell, a chromosome, a nucleic acid, a protein, a DNA, a RNA, a fragment of DNA, a fragment of RNA, and a fragment of protein.

7. The method of flow cytometry as described in claim 1, further comprising the step of locating said variable volume container in a receptacle.

8. The method of flow cytometry as described in claim 7, wherein said step of exerting an amount of pressure with an amount of a gas on an exterior surface of said flexible wall of said variable volume container further comprises the step of collecting said amount of gas between an interior surface of said receptacle and said exterior surface of said variable volume container.

9. The method of flow cytometry as described in claim 1, wherein said step of illuminating said particle in said one of said plurality of droplets for a duration of time comprises the step of illuminating said particle in said one of said plurality of droplets with at least one laser beam.

10. The method of flow cytometry as described in claim 1, wherein said step of detecting an emission generated by said particle which varies based upon corresponding variation of at least one particle characteristic of said particle comprises the step of detecting a fluorescent emission which varies based upon a difference in an amount of DNA within a cell.

11. The method of flow cytometry as described in claim 1, further comprising the step of sorting said particle based upon relative presence or absence of said at least one particle characteristic.

12. The method of flow cytometry as described in claim 11, wherein said step of sorting said particle based upon relative presence or absence of said at least one particle characteristic comprises the step of sorting X-chromosome bearing sperm cells from Y-chromosome bearing sperm cells.

13. The method of flow cytometry as described in claim 1, further comprising the step of providing said flexible wall with at least two layers.

14. The method of flow cytometry as described in claim 13, further comprising the step of providing a first layer compatible with said amount of gas and providing a second layer compatible with said fluid.

15. The method of flow cytometry as described in claim 14, further comprising the step of collecting said amount of gas between said first layer and said second layer.

16. The method of flow cytometry as described in claim 15, further comprising the step of bonding said first layer to said second layer.

17. The method of flow cytometry as described in claim 16, wherein said first layer comprises a material selected from the group consisting of polypropylene, a polyethylene, a fluorocarbon, a styrene, and a polycarbonate.

18. The method of flow cytometry as described in claim 17, wherein said second layer comprises a material selected from the group consisting of polypropylene, a polyethylene, a fluorocarbon, a styrene, and a polycarbonate.

19. The method of flow cytometry as described in claim 16, further comprising providing at least one intermediate material layer between said first layer and said second layer.

* * * * *

UNITED STATES PATENT AND TRADEMARK OFFICE
CERTIFICATE OF CORRECTION

| | | |
|---|---|---|
| PATENT NO. | : 8,080,422 B2 | |
| APPLICATION NO. | : 12/807231 | |
| DATED | : December 20, 2011 | |
| INVENTOR(S) | : Edwin Dean Neas et al. | |

It is certified that error appears in the above-identified patent and that said Letters Patent is hereby corrected as shown below:

In the Claims:

Column 18, In Claim 4, line 5 "a cleaning solutions" should read --a cleaning solution--.

Column 18, In Claim 5, line 7 "a helium gas" should read --and a helium gas--.

Column 20, In Claim 18, line 3 "polypropylene" should read --a polypropylene--.

Signed and Sealed this
Fifth Day of June, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,080,422 B2 | Page 1 of 1 |
| APPLICATION NO. | : 12/807231 | |
| DATED | : December 20, 2011 | |
| INVENTOR(S) | : Edwin Dean Neas et al. | |

It is certified that error appears in the above-identified patent and that said Letters Patent is hereby corrected as shown below:

In the Claims:

Column 18, line 9 (Claim 4, line 5) "a cleaning solutions" should read --a cleaning solution--.

Column 18, line 17 (Claim 5, line 7) "a helium gas" should read --and a helium gas--.

Column 20, line 1 (Claim 18, line 3) "polypropylene" should read --a polypropylene--.

This certificate supersedes the Certificate of Correction issued June 5, 2012.

Signed and Sealed this
Third Day of July, 2012

David J. Kappos
*Director of the United States Patent and Trademark Office*